(12) United States Patent
Schwartz

(10) Patent No.: US 6,371,759 B1
(45) Date of Patent: Apr. 16, 2002

(54) THERMOFORMED PLASTIC DENTAL RETAINER AND METHOD OF CONSTRUCTION

(75) Inventor: Dann A. Schwartz, Kenner, LA (US)

(73) Assignee: Raintree Essix, Inc., Metairie, LA (US)

( * ) Notice: Subject to any disclaimer, the term of this patent is extended or adjusted under 35 U.S.C. 154(b) by 0 days.

(21) Appl. No.: 09/568,727

(22) Filed: Oct. 6, 2000

(51) Int. Cl.⁷ .................................................. A61C 3/00
(52) U.S. Cl. .............................. 433/6; 128/861; 264/16
(58) Field of Search .............................. 433/6; 128/859, 128/861, 862; 264/16

(56) References Cited

U.S. PATENT DOCUMENTS

| 3,666,849 A | * | 5/1972 | Williams et al. |
| 3,744,262 A | * | 7/1973 | Bose |
| 3,899,072 A | * | 8/1975 | Reinhart |
| 3,919,378 A | * | 11/1975 | Smarook |
| 4,070,515 A | * | 1/1978 | Smarook |
| 4,517,043 A | * | 5/1985 | Martin et al. |
| 5,692,894 A | * | 12/1997 | Schwartz et al. ............... 433/6 |

* cited by examiner

Primary Examiner—Ralph A. Lewis
(74) Attorney, Agent, or Firm—John M. Harrison

(57) ABSTRACT

A thermoformed plastic dental retainer and method of construction including rapid cooling of the retainer, typically using a refrigerant coolant, as the retainer sets on a dental impression cast. The dental retainer is constructed by first forming an impression of a patient's upper or lower dentition and constructing the cast from the impression The retainer is vacuum-thermoformed over the cast using a sheet, plate or disc of thermoformable plastic and a vacuum or pressure thermoforming machine. As the thermoformed plastic retainer sets on the cast, the retainer is rapidly cooled typically by spraying a refrigerant coolant on the retainer. This step causes the retainer to thermally contract against and precisely conform to the configuration and texture of the cast for an accurate and tight fit of the retainer on the patient's dentition Protrusions or divots may be formed in the retainer to apply repositioning pressure to maloccluded or crooked teeth while the retainer is worn on the patient's dentition over a period of days or weeks.

1 Claim, 2 Drawing Sheets

THERMOFORMED PLASTIC DENTAL RETAINER AND METHOD OF CONSTRUCTION

BACKGROUND OF THE INVENTION

1. Field of the Invention

This invention relates to dental retainers or appliances for straightening and retaining teeth and more particularly, to a thermoformed plastic dental retainer and method of construction including rapid, typically refrigerant-induced cooling of the retainer as the retainer sets on a dental impression cast which is constructed from an impression of a patient's upper or lower dentition. Using a sheet, plate or disc of thermoformable plastic and a vacuum or pressure thermoforning machine, the retainer is initially vacuum-thermoformed over the dental impression cast. As the thermoformed plastic retainer sets on the cast, a refrigerant coolant, particularly 1,1,1,2-tetrafluoroethane, is typically sprayed on the retainer. The rapid cooling of retainer on the cast, induced by the coolant, causes the retainer to thermally contract against the cast and precisely conform to the configuration and texture of the cast, and thus fit more accurately and tightly on the patient's dentition during treatment. Protrusions or divots may be formed in the retainer and gaps, openings or windows formed in the retainer on the opposite sides of the respective divots to accommodate unhindered tooth repositioning movement as the divots apply repositioning pressure to malocculded or crooked teeth while the retainer is worn on the patient's dentition over a period of days or weeks.

2. Description of the Prior Art

A "Thermoformed Plastic Dental Retainer and Method of Construction" is described in my U.S. Pat. No. 5,692,894, dated Dec. 2, 1997. The dental retainer is constructed by first forming an impression of a patient's upper or lower dentition and constructing a cast from the impression The retainer is vacuum thermoformed over the cast using a sheet, plate or disc of thermoformable plastic and a vacuum or pressure thermoforming machine. A protrusion or divot is formed in the retainer on the labial or lingual side of each tooth which is to be repositioned lingually or labially, respectively, and a gap, opening or window is formed in the retainer on the opposite side of the divot to accommodate unhindered tooth repositioning movement. As the retainer is worn on the patient's dentition over a period of days or weeks, the projecting divots apply pressure to the respective teeth and push the teeth into the gap or window of the retainer to a straightened position. By appropriately positioning the divots in the retainer with respect to the patient's malpositioned teeth, the teeth can be moved labially, lingually or rotated, as needed, for straightening.

The thermoformable plastic dental retainer described in my U.S. Pat. No. 5,692,894 represents a considerable improvement over conventional teeth straightening and retaining devices, in several respects. The retainer can be used to retain the dentition of finished orthodontic cases at a fraction of the cost and with fewer problems than conventional devices. Unlike conventional wire braces, the clear retainer is aesthetically-pleasing to the patient and usually requires no periodic adjustment, thus affording the clinician significant relief in chair time and administrative detail It has surprisingly been found that rapidly cooling the thermoformed retainer as the retainer sets on the cast, such as by spraying a refrigerant coolant on the retainer, causes thermal contraction of the retainer against the cast and the retainer to more precisely conform to the configuration and texture of the cast and thus, the patient's mouth than is the case when the cooling step is omitted. The retainer thus more accurately fits in the patient's mouth throughout extended wearing of the retainer during treatment.

It is therefore an object of this invention to provide a new and improved thermoformed plastic dental retainer and method of construction of the retainer.

Another object of this invention is to provide a new and improved thermoformed plastic dental retainer which more precisely conforms to the configuration and texture of a patient's dentition.

Still another object of this invention is to provide a thermoformed plastic dental retainer and method of construction the retainer including rapidly cooling the thermoformed retainer as the retainer sets on a dental impression cast constructed from an impression of a patient's upper or lower dentition.

Yet another object of this invention is to provide a thermoformed plastic dental retainer and method of construction of the dental retainer, including forming an impression of a patient's upper or lower dentition and constructing a cast from the impression; vacuum-thermoforming the retainer over the cast using a sheet, plate or disc of thermoformable plastic and a vacuum or pressure thermoforming machine; and rapidly cooling the retainer typically by applying a refrigerant coolant to the retainer as the retainer sets on the cast, whereby the rapidly-cooling retainer thermally contracts against the dental impression cast and precisely conforms to the configuration and texture of the cast, to accurately and snugly fit on the patient's dentition during treatment.

SUMMARY OF THE INVENTION

These and other objects of the invention are provided in a thermoformed plastic dental retainer and method of construction including rapid cooling of the retainer, typically using a refrigerant coolant, as the retainer sets on a dental impression cast. The dental retainer is constructed by first forming an impression of a patient's upper or lower dentition and constructing a cast from the impression. The retainer is vacuum-thermoformed over the cast using a sheet, plate or disc of thermoformable plastic and a vacuum or pressure thermoforming machine. As the thermoformed plastic retainer sets on the cast, the retainer is rapidly cooled typically by spraying a refrigerant coolant, such as 1,1,1,2-tetrafluoroethane, on the retainer. This step causes thermal contraction of the rapidly-cooling retainer against the cast, and the retainer precisely conforms to the configuration and texture of the cast and thus, achieves a more accurate and tighter fit on the patient's dentition during treatment. Protrusions or divots may be formed in the retainer and gaps, openings or windows formed in the retainer on the opposite sides of the respective divots to accommodate unhindered tooth repositioning movement as the divots apply corrective pressure to malocculded teeth while the retainer is worn on the patient's dentition over a period of days or weeks.

BRIEF DESCRIPTION OF THE DRAWINGS

The invention will be better understood by reference to the accompanying drawing, wherein.

DESCRIPTION OF THE PREFERRED EMBODIMENTS

Figure 3:
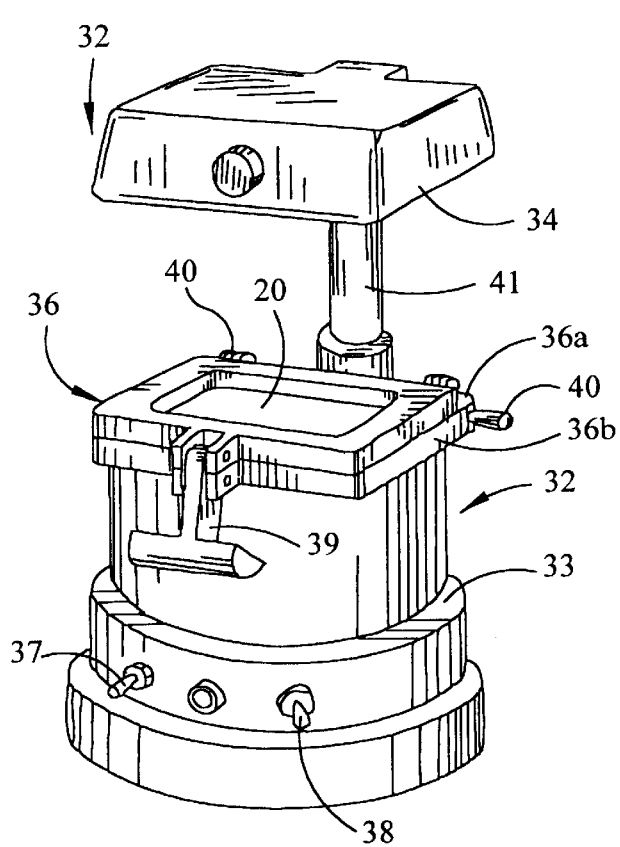
FIG. 3 is a perspective view of a standard or conventional vacuum thermoforming machine used in forming the thermoformed plastic dental retainer of this invention on a dental impression cast.
Figure 4:
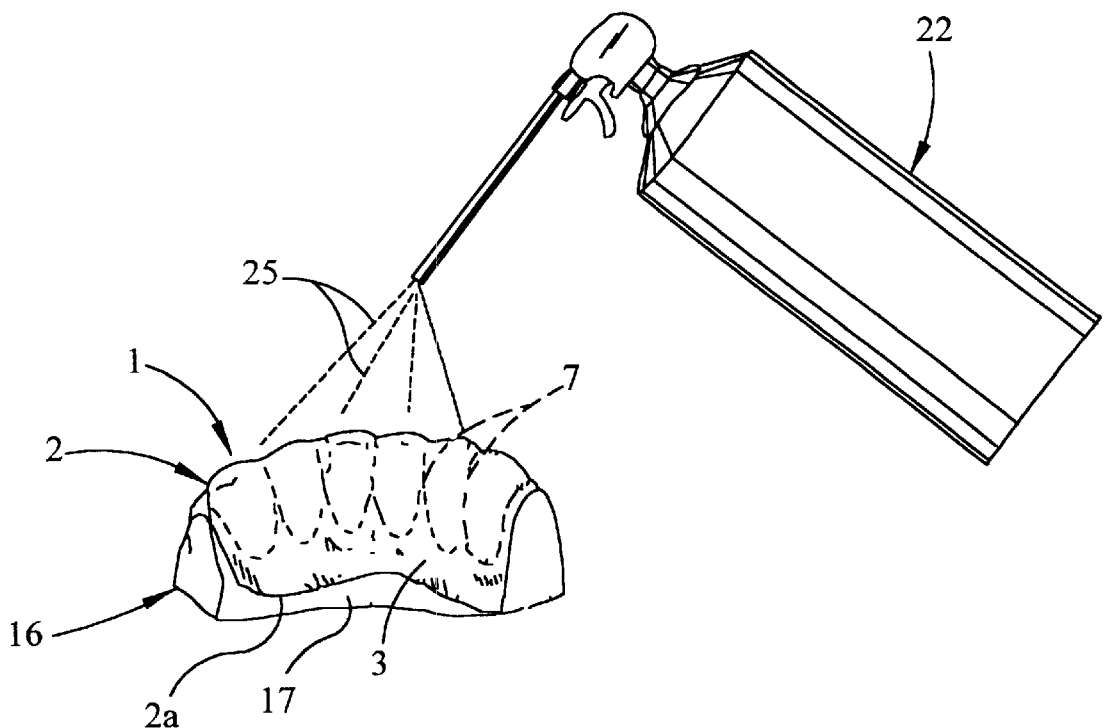
FIG. 4 is a perspective view of a preferred embodiment of the thermoformed plastic dental retainer, more particularly illustrating spraying of a refrigerant coolant on the retainer as the retainer sets on the dental impression cast.
Figure 5:
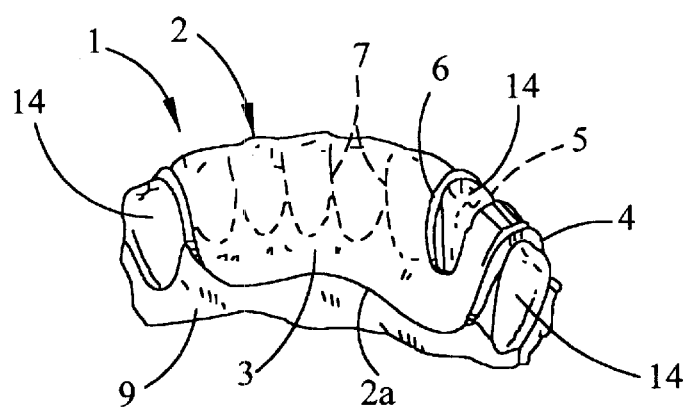
FIG. 5 is a perspective view of the thermoformed plastic dental retainer, more particularly illustrating the retainer engaging a patient's lower anterior dentition, with a divot and window combination in place in the retainer.

Referring initially to FIGS. 1–5 of the drawings, the thermoformed plastic dental retainer, hereinafter referred to as the retainer, of this invention is generally illustrated by reference numeral 1. The retainer 1 is characterized by a retainer body 2, vacuum-formed from a sheet or plate of thermoformable plastic material 20 (FIG. 3) on a dental impression cast 16, illustrated in FIG. 2. The dental impression cast 16 is formed from a conventional dental impression tray 12 shown in FIG. 1, using a pressure machine (not illustrated) or a conventional vacuum thermoforming machine 32 (illustrated in FIG. 3), as hereinafter futher described. The retainer body 2 is characterized by multiple tooth impressions 7, corresponding to the respective teeth of the patient's lower anterior dentition and illustrated in phantom in FIGS. 4 and 5. The retainer body 2 includes a lingual surface 3, which, during retainer use, covers the lingual gingiva 9 of the dentition, as illustrated in FIG. 5, and a facial or labial surface 4, which covers the labial surface (not illustrated) of the dentition. Projecting divots 5 (illustrated in phantom in FIG. 5) are typically formed in the labial or lingual surface of the retainer body 2 and extend into the plastic tooth impressions 7 corresponding to teeth which are in need of repositioning, as hereinafter further described. Accordingly, openings or windows 6 are cut in the retainer body 2 on the opposite labial or lingual side from the respective divots 5, to accommodate repositioning movement of the teeth in the tooth socket (not illustrated), as the divots 5 apply constant repositioning pressure to the respective teeth 14 while the retainer 1 is worn on the dentition over a period of time, as illustrated in FIG. 5. The retainer body 2 is maintained in position on the patient's dentition by snugly engaging or "snapping into" the natural undercuts below the contact points of adjacent teeth, and may be removed as desired.

Figure 1:
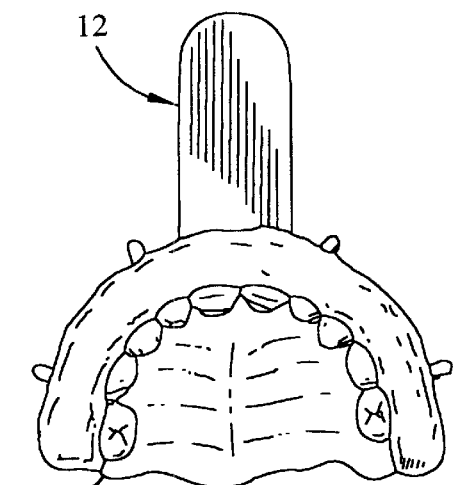
FIG. 1 is a top view of a patient's dental impression, formed in a standard or conventional dental impression tray.
Figure 2:
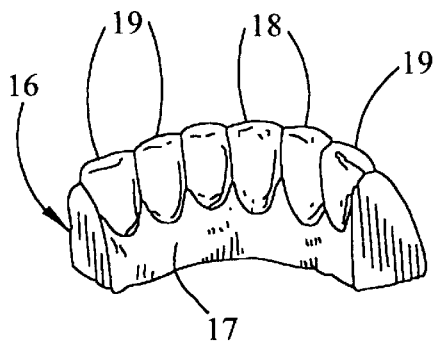
FIG. 2 is a perspective view of a dental impression cast formed from a dental impression, taken from the lower anterior dentition of a patient.

Referring now to FIGS. 1–3 of the drawings, the retainer 1 is constructed by first making a dental impression 13 of the patient's upper or lower dentition, or both, preferably using a precision impression material such as polyvinyl siloxane and a standard or conventional dental impression tray 12, illustrated in FIG. 1. A dental impression cast 16 is then made from that portion of the dental impression 13 corresponding to the area of malpositioned teeth, usually the anterior dentition, or that portion of the dentition extending from the left canine to the right canine, as illustrated in FIG. 2. The dental impression cast 16 includes a lingual surface 17, a labial surface (not illustrated) and cast teeth 18. Preparatory to forming the retainer 1, the dental impression cast 16 typically is dried thoroughly and trimmed such that the occlusal surfaces 19 of the cast teeth 18 have a slanted or tapered configuration, as further illustrated in FIG. 2, to facilitate easy removal of the retainer body 2 from the dental impression cast 16. Because the retainer 1 is maintained in position on the patient's dentition by "snapping into" the multiple undercuts below the contact points of adjacent teeth, the undercuts on the dental impression cast 16 may need trimming for augmentation if their presence on the dental impression cast 16 is not evident. As illustrated in FIG. 3, a standard or conventional pressure machine or a vacuum thermoforming machine 32, having a base 33 with a perforated top vacuum plate (not illustrated) and a heating unit 34 extending from the base 33 and mounted on a frame post 41 and energized by a heater switch 37, is used to vacuum thermoform a retainer body 2 having tooth impressions 7 matching the cast teeth 18 of the dental impression cast 16. The vacuum thermoforming machine 32 also includes a slidable frame 36 having a top frame member 36a hinged to a bottom frame member 36b. The top frame member 36a is removably latched to the bottom frame member 36b by means of a frame latch knob 39. A vacuum motor (not illustrated) is contained in the base 33 and energized by a vacuum motor switch 38. Alternatively, a conventional pressure thermoforming machine (not illustrated) can be used to shape the retainer body 2 over the dental impression cast 16 according to the knowledge of those skilled in the art.

The retainer body 2 is formed on the dental impression cast 16 by first energizing the heating unit 34 of the vacuum thermoforming machine 32 by means of the heater switch 37. The dental impression cast 16 is then placed on the perforated vacuum plate (not illustrated) on the top of the base 33, with the cast teeth 18 of the dental impression cast 16 facing upwardly. Before the frame 36 is raised on the frame post 41 by means of frame lift knobs 40 to within a suitable heating distance of the heating unit 34, the top frame member 36a is pivoted upwardly with respect to the bottom frame member 36b. A thermoformable plastic plate 20, preferably constructed of ESSIX (trademark) type C plastic sold by RAINTREE ESSIX (trademark), Inc., of New Orleans, La., is next centered on the bottom frame member 36b. The top frame member 36a is then pivoted downwardly and secured by means of the frame latch knob 39, and the frame 36 is raised on the frame post 41 such that the thermoformable plastic plate 20 is located immediately beneath the heating unit 34. After approximately 25 to 50 seconds, the thermoformable plastic plate 20 is heated to a suitable thermoforming temperature and typically begins to sag slightly, but should not be heated to a temperature such that it is allowed to sag about ½ inch or more. The vacuum motor in the base 33 is then energized by means of the vacuum motor switch 38, and the frame 36 is rapidly lowered on the frame post 41 over the vacuum plate of the base 33 by means of the frame lift knobs 40, such that the softened thermoformable plastic plate 20 is first draped and then tightly vacuum-pulled over the dental impression cast 16. After ten to fifteen seconds, the retainer body 2 has been formed from the thermoformable plastic plate 20, and the heating unit 34 is turned off. Immediately after thermoforming the retainer body 2 on the dental impression cast 16, the retentive proximal undercuts in the retainer body 2 can be enhanced, as needed, typically by using an ESSIX ACCENTUATOR (trademark) while the plastic retainer body 2 remains formable.

Referring next to FIGS. 4 and 5 and initially to FIG. 4 of the drawings, as the retainer body 2 begins to set and cool on the dental impression cast 16, the retainer body 2 is rapidly cooled typically by spraying the entire retainer body 2 with an aerosol refrigerant coolant 25, typically from a refrigerant coolant aerosol can 22. Typically, the aerosol refrigerant coolant 25 is that sold by RAINTREE ESSIX (trademark), Inc., of New Orleans, La., under the trademark FREEZE SPRAY, which contains 1,1,1,2-tetrafluoroethane. The rapid cooling of the retainer body 2, imparted by the refrigerant coolant 25, causes the retainer body 2 to quickly thermaly contract against the dental impression cast 16. This sudden thermal contraction of the retainer body 2 causes the impressionable plastic of the retainer body 2 to conform to the configuration and texture of the dental impression cast 16, including that portion of the dental impression cast 16 corresponding to the natural undercuts of the patient's dentition. Accordingly, the retainer body 2 is complementary to the configuration and texture of the patient's dentition and after removal of the retainer body 2 from the dental impression cast 16, the retainer body 2 is capable of achieving a more accurate and tighter fit on the patient's dentition than would be the case if the cooling step of the retainer body 2 were omitted and the retainer body 2 allowed to cool gradually on the dental impression cast 16. Preferably, the refrigerant coolant 25 is sprayed on the retainer body 2 as soon as possible after thermoforming the retainer body 2 on the dental impression cast 16 as heretofore described, in order to prevent "lingual lift-off", or lifting of the lingual gingival edge 2a of the plastic retainer body 2 from the dental impression cast 16. If "lingual lift-off" of the retainer body 2 from the dental impression cast 16 does occur, the lingual gingival edge 2a of the plastic retainer body 2 can be modified to conform to the patient's gingiva typically using crimping pliers, according to the knowledge of those skilled in the art. It will be appreciated by those skilled in the art that a divot or divots 5 (illustrated in phantom in FIG. 5) can be formed in the labial surface 4, as illustrated, or the lingual surface 3 of the retainer body 2, adjacent to a maloccluded tooth or teeth 14 of the patient's dentition and a window or windows 6 cut in the lingual surface 3 or labial surface 4, respectively, opposite each divot or divots 5, typically in the manner described in my U.S. Pat. No. 5,692,894. As the retainer body 2 is worn on the patient's dentition over a period of days or weeks, the divots 5 apply a selected biomechanical force on the respective malpositioned teeth 14, and the corresponding windows 6 adjacent to the teeth 14 accommodate repositioning of the teeth 14 responsive to pressure applied by the divots S on the teeth 14. Alternatively, the retainer body 2 can be worn on a patient's dentition a selected tooth or teeth of which have been straightened by conventional orthodontic methods, to retain the straightened tooth or teeth in the dentition over an appropriate period of time.

It will be appreciated by those skilled in the art that the thermoformable plastic dental retainer when constructed according to the method of this invention is capable of an accurate, tight and comfortable fit of the retainer on a patient's dentition during prolonged or short-term treatment of maloccluded or crooked teeth or retention of straightened teeth. While the cooling step of the retainer on the dental impression cast has been described above as utilizing an aerosol refrigerant coolant containing 1,1,1,2-tetrafluoroethane, it is understood that any type of suitable coolant known to those skilled in the art can be applied to the retainer to induce the rapid cooling and contraction of the retainer on the dental impression cast. Moreover, it is understood that rapid cooling and thermal contraction of the retainer on the dental impression cast can be induced using any suitable means known to those skilled in the art other than spraying the retainer with the coolant, including applying cold water to the retainer as the retainer sets on the cast, although best results are achieved by applying the refrigerant coolant to the retainer. It is also understood that while the dental retainer of this invention can be constructed using any type of thermoformable plastic known to those skilled in the art, the preferred plastic is ESSIX (trademark) type C plastic sold by RAINTREE ESSIX (trademark), Inc., of New Orleans, La, as indicated above, since this type of plastic is substantially impervious to abrasion and is ideal for long-term use or for nocturnally-bruising or grinding patients. While the material of choice for the dental impression is a precision impression material such as polyvinyl siloxane, it is understood that alienate can be used for the impression as long as the dental impression cast is poured within about 5 minutes of forming the impression.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, what is claimed is:

1. A method of constructing a dental retainer having a retainer body, comprising:
   (a). maling an impression of a patient's dentition;
   (b). constructing a dental impression cast of said impression;
   (c). vacuum-thermoforming a sheet of thermoformable plastic on said dental impression cast; and
   (d). rapidly cooling said sheet of thermoformable plastic as said sheet of thermoformable plastic sets on said dental impression cast by applying a refrigerant coolant to freeze said sheet of thermoformable plastic on said dental impression cast whereby said sheet of thermoformable plastic thermally contracts against said dental impression cast and substantially conforms to the configuration and texture of said dental impression cast to form said retainer body.

* * * * *